US00PP22705P3

(12) United States Plant Patent
Kelaidis

(10) Patent No.: US PP22,705 P3
(45) Date of Patent: May 1, 2012

(54) ***OSTEOSPERMUM* PLANT NAMED 'AVALANCHE'**

(50) Latin Name: ***Osteospermum* sp.**
Varietal Denomination: Avalanche

(75) Inventor: Panayoti Kelaidis, Denver, CO (US)

(73) Assignee: Plant Select, Fort Collins, CO (US)

( * ) Notice: Subject to any disclaimer, the term of this patent is extended or adjusted under 35 U.S.C. 154(b) by 0 days.

(21) Appl. No.: 12/804,079

(22) Filed: Jul. 13, 2010

(65) Prior Publication Data

US 2012/0017342 P1 Jan. 19, 2012

(51) Int. Cl.
*A01H 5/00* (2006.01)

(52) U.S. Cl. ..... Plt./360

(58) Field of Classification Search ..... Plt./360
See application file for complete search history.

*Primary Examiner* — June Hwu
*Assistant Examiner* — Louanne Krawczewicz Myers
(74) *Attorney, Agent, or Firm* — Jondle & Associates, P.C.

(57) ABSTRACT

An *Osteospermum* variety named 'Avalanche' particularly distinguished by a cold hardiness to −25° F., a large, white flower size and a compact, prostrate habit, is disclosed.

1 Drawing Sheet

Genus and species: *Osteospermum* sp.

Variety denomination: 'Avalanche'.

BACKGROUND OF THE NEW PLANT

The present invention comprises a new and distinct variety of *Osteospermum*, botanically known as *Osteospermum* sp., and hereinafter referred to by the variety name 'Avalanche'. The new variety originated from an *Osteospermum jucundum* (unpatented) and *Osteospermum barberiae* (unpatented) hybridization. Cuttings from the hybridization were rooted, planted and grown out in Denver, Colo. in August 2002. 'Avalanche' was selected in June 2005 based on its extreme cold hardiness, large, white flowers and compact, prostrate habit. 'Avalanche' was first propagated asexually by vegetative cuttings in June 2005 in Denver, Colo. and has been asexually propagated over multiple generations. The present invention has been found to be stable and reproduce true to type through successive asexual propagations via vegetative cuttings.

Plant Breeder's Rights for this variety have not been applied for. 'Avalanche' has not been made publicly available or sold more than one year prior to the filing date of this application.

SUMMARY OF THE INVENTION

The following are the most outstanding and distinguishing characteristics of the new variety when grown under normal horticultural practices in Denver, Colo.

1. Cold hardiness to −25° F.;
2. Large, white flowers; and
3. Compact, prostrate habit.

DESCRIPTION OF THE PHOTOGRAPH

This new *Osteospermum* plant is illustrated by the accompanying photograph which shows an overall view of a mature plant. The colors shown are as true as can be reasonably obtained by conventional photographic procedures. The photograph was taken in June 2009 of a three-year-old plant in a garden in Denver, Colo. under conditions, which approximate those generally used in commercial practice.

DESCRIPTION OF THE NEW VARIETY

The following detailed descriptions set forth the distinctive characteristics of 'Avalanche'. The data which define these characteristics were collected from asexual reproductions carried out in Denver, Colo. The plant history was taken in Spring 2010 on plants rooted from cuttings stuck in December 2009. The rooted cuttings were transplanted and planted in larger pots (one gallon size) in February 2010 in a greenhouse. Color readings were taken under natural light as well as microscope light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:

*Family.*—Compositae.

*Botanical.*—*Osteospermum* sp.

*Common.*—*Osteospermum* , Cape Daisy, South African Daisy.

*Designation.*—'Avalanche'.

Parentage:

*Female parent.*—*Osteospermum jucundum* (unpatented).

*Male parent.*—*Osteospermum barberiae* (unpatented).

Plant description:

*Habit.*—Caespitose; compact, prostrate.

*Life cycle.*—Perennial.

*Form.*—Stems spreading at ground level or just above ground level.

*Height (from soil line to top of foliage).*—14.5 cm.

*Width.*—30.0 cm (Potted plant, can get larger in garden).

*Cold tolerance.*—Cold hardiness to −25° F.

Stems:

*General.*—Multiple stems, circular in cross section.

*Stem length (total).*—32.5 cm.

*Diameter.*—0.3 cm on flower stem midway up.

*Internode length.*—1.0 cm on average, some longer some shorter.

*Color.*—RHS 154C (Yellow-green).

*Pubescence.*—On flower stems only.

*Color.*—Translucent and colorless.

*Shape.*—Glandular, but not hooked or barbed.

Branches:

*General.*—Circular in cross section.

*Number of main branches.*—6 on potted plant, many more main branches in the ground.

*Total number of branches.*—15 on potted plant, many more branches in the ground.

*Length.*—Approximately 1.0 cm from soil line to first node, 1.0 cm between first and second nodes.

*Diameter.*—0.5 cm.

*Internode length.*—0.7 cm.

*Color.*—RHS 145C (Yellow-green).

*Pubescence.*—Absent.

Leaves:

*Arrangement.*—Alternate.

*Shape.*—Oval, toothed.

*Apex.*—Acuminate.

*Base.*—Attenuate.

*Margin.*—Ciliate (hairs limited to margin of the leaf).

*Venation.*—Pinnipalmate.

*Surface (both surfaces).*—Glabrous.

*Surface pubescence (both surfaces)*: Ciliate (on edge of leaf only).

*Pubescence color (both surfaces).*—Translucent and colorless.

*Attachment.*—Attenuate.

*Length.*—3.5 cm.

*Width.*—0.4 cm.

*Thickness.*—0.1 cm.

*Color.*—Upper surface: RHS 147A (Yellow-green). Lower surface: RHS 137A (Green).

*Venation color.*—Upper surface: Main vein is RHS 148D (Yellow-green). Lower surface: Main vein is RHS 147A (Yellow-green).

Inflorescence:

*Number per plant.*—Varies from 1 to 40 depending on the size of the plant.

*Type.*—Capitulum (head); disc florets are perfect and ray florets are carpellate.

*Flowering habit.*—Heavy production in late spring to early summer, less production through the rest of growing season but the plant will often have at least a bloom or two at any one time.

*Lastingness of flowers.*—5 to 7 days, under normal conditions.

*Fragrance.*—Absent.

*Flower bud.*—Diameter: Range from 1.1 cm to 1.2 cm. Length: 1.2 cm. Form: Spherical. Color: Closest to RHS 137A (green).

*Inflorescence length.*—3.7 cm.

*Inflorescence diameter.*—Average 3.3 cm; range of 2.7 cm to 3.6 cm.

*Petal (ray floret) number.*—16 per inflorescence.

*Disc diameter.*—1.5 cm.

*Disc floret number.*—Approximately 45 per inflorescence.

*Peduncle length.*—16.5 cm from inflorescence to first node.

*Peduncle diameter.*—0.4 cm.

*Peduncle color.*—RHS 154C (Yellow-green).

*Peduncle texture.*—Dull, slight pubescence.

*Receptacle.*—Height: 4.0 mm. Diameter: 7.0 mm. Shape: Flat on top, goblet shaped (cupule).

*Phyllaries.*—Arrangement: per inflorescence, free, arranged symmetrically. Length: 1.4 cm to 1.5 cm. Width: 0.1 cm. Apex: Acute. Base: Aequilateral and lanceolate, pubescent.

*Margin.*—Ciliate.

*Shape.*—Narrowly elliptic.

*Color.*—Upper surface: RHS 139A (Green). Lower surface: RHS 138A (Green).

*Texture.*—Upper surface: Hirsutulous with glandular hairs. Lower surface: Glandular hair present.

Ray florets (ligules):

*Corolla.*—One petal per ray floret; only the outer row of florets are the ray florets.

*Number of ray florets.*—16 per inflorescence.

*Length.*—3.3 cm.

*Width.*—1.0 cm at widest point of petal.

*Shape.*—Elliptic (ligulate).

*Apex.*—Obcordate with 3 points.

*Base.*—Ligulate, partially fused at the base.

*Margin.*—Smooth.

*Color.*—Upper surface: Closest to RHS 155C (White) with RHS 66D (Red-purple) at apex and margins when first opening. Lower surface: Largest part is RHS 142D (Green).

*Texture.*—Upper surface: Smooth with ridges, some large plications visible with naked eye. Lower surface: Smooth except for hairs at very base wrapping around to upper surface.

*Pubescence.*—Only at base, glands on upper portions of petal.

Disc florets:

*Color.*—RHS 3D (Yellow).

*Shape.*—Tubular.

*Apex.*—Acute.

*Surface.*—Glandular.

*Size.*—Length: 1.1 cm. Width: 0.4 cm.

Reproductive organs:

*Pistil length.*—0.4 cm in ray florets.

*Stigma color.*—RHS 202A (Black) in ray florets.

*Stigma shape.*—Cleft in two.

*Style color.*—RHS 196C (Greyed-green) in ray florets.

*Style length.*—Approximately 7.0 mm.

*Ovary.*—Superior in disc florets. Quantity: Average of 87.25; range of 79 to 92 in disk flowers. Size: 4.0 mm×2.0 mm×<1.0 mm. Color: Margins darkest and center palest; range from RHS 145A to RHS 145D (Yellow-green).

*Pistil form.*—One style with two stigma branches in disc florets.

*Stamens.*—5, fused into a single tube in disc florets. Anther color: RHS 202A (Black) in disc florets. Pollen amount: Little, several grains per floret. Pollen color: RHS 14A (Yellow-orange) in disc florets. Filament color: RHS 3D (Yellow) in disc florets.

Fruit and seed set: None observed

Disease and insect resistance: None

COMPARISON WITH PARENTAL AND COMMERCIAL VARIETIES

'Avalanche' differs from the female parent, the *Osteospermum jucundum* (unpatented), in that 'Avalanche' has large blooms that are white in color, while *Osteospermum jucundum* has small blooms that are pink in color.

'Avalanche' differs from the male parent, the *Osteospermum barberiae* (unpatented), in that 'Avalanche' has white flower and a compact, short plant habit, while *Osteospermum barberiae* has purple-pink flowers and a tall plant habit.

'Avalanche' differs from the commercial *Osteospermum variety* 'Oste Whitey' (unpatented) in that 'Avalanche' is cold hardy to −25° F. and a prostrate plant habit with leaves that are entire, while 'Oste Whitey' is frost tender at 28° F. and has a shrubby plant habit with serrated leaves.

We claim:

1. A new and distinct variety of *Osteospermum* plant named 'Avalanche' as shown and described herein.

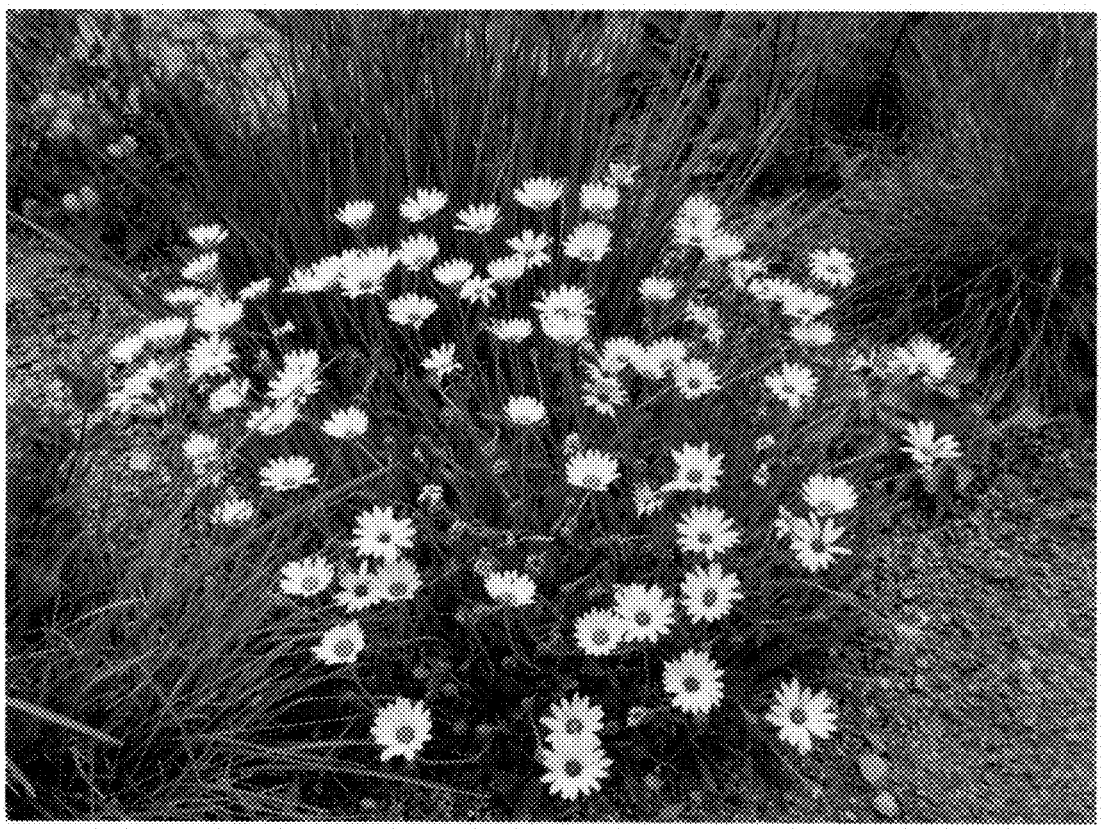

* * * * *